United States Patent [19]

Tuominen et al.

[11] Patent Number: 4,695,453

[45] Date of Patent: Sep. 22, 1987

[54] THICKENED ALCOHOLIC ANTIMICROBIAL COMPOSITIONS

[75] Inventors: Francis W. Tuominen, Minneapolis; Helmut K. Maier, Golden Valley; Warren W. Howland, Champlin, all of Minn.

[73] Assignee: Henkel Corporation, Ambler, Pa.

[21] Appl. No.: 858,099

[22] Filed: Apr. 30, 1986

Related U.S. Application Data

[63] Continuation of Ser. No. 694,538, Jan. 24, 1985, abandoned.

[51] Int. Cl.$^4$ .............................................. A61K 31/78
[52] U.S. Cl. ...................................... 424/81; 424/78; 514/724; 514/730; 524/379; 524/547
[58] Field of Search ............... 424/78, 81; 524/379, 524/547; 514/724, 730

[56] References Cited

U.S. PATENT DOCUMENTS

| | | | |
|---|---|---|---|
| 3,692,673 | 9/1972 | Hoke | 526/240 |
| 3,931,089 | 1/1976 | Karl | 524/300 |
| 4,065,422 | 12/1977 | Lundmark et al. | 524/394 |
| 4,412,026 | 10/1983 | Collins | 524/354 |
| 4,412,027 | 10/1983 | Klein et al. | 524/364 |

OTHER PUBLICATIONS

Condensed Chemical Dictionary, 10th ed; Hawley, p. 121.
Rheothik Polymer 80-11; Henkel Corporation; pp. 1-6.
Condensed Chemical Dictionary, 10th ed., Hawley p. 795.

*Primary Examiner*—Joseph L. Schofer
*Assistant Examiner*—J. M. Reddick
*Attorney, Agent, or Firm*—Ernest G. Szoke; Patrick J. Span

[57] ABSTRACT

A thickened alcoholic antibacterial composition is provided which contains as a thickener a polymer having as the recurring structural unit an acrylamidoalkanesulfonic acid monomer or ammonium salt thereof. Methods of thickening an alcoholic antibacterial composition and methods of controlling bacteria with such compositions are also provided.

4 Claims, No Drawings

THICKENED ALCOHOLIC ANTIMICROBIAL COMPOSITIONS

This application is a continuation application of co-pending application Ser. No. 694,538 filed on Jan. 24, 1983, now abandoned.

FIELD OF THE INVENTION

This invention relates to alcoholic antibacterial compositions thickened with a synthetic polymer. More particularly, this invention relates to alcoholic antibacterial compositions thickened by a polymer comprised of an acrylamidoalkanesulfonic acid monomer or the ammonium salt thereof.

BACKGROUND OF THE INVENTION

U.S. Pat. No. 3,931,089 discloses a homopolymer of 2-acrylamido-2-methylpropanesulfonic acid or its salts is stable as a thickener in highly acidic aqueous solutions which may also contain a 2-3 carbon alcohol. The patent discloses that the acid homopolymer and the alkali and alkaline earth metal salts of the homopolymer are very soluble in strong acid solutions.

U.S. Pat. No. 4,065,422 to Lundmark, et al., discloses that homopolymers of salts of 2-acrylamido-2-methylpropanesulfonic acid impart lubricity to alcohol base compositions. The patent discloses that the homopolymers of salts which contain as cations sodium, potassium, ammonium, monoethanolamine, diethanolamine, triethanolamine, and 2amino-2-methyl-1-propanol are water soluble polymers and that homopolymers of the salts, calcium and magnesium, are water-insoluble.

U.S. Pat. No. 4,065,422 states that the alcohols useful in the compositions of that invention are the $C_1$-$C_{24}$ alcohols such as methanol, ethanol, isopropanol, propyl, lauryl, myristyl, cetyl and stearyl alcohols, as well as mixtures thereof. The patent goes on to state that the polymers of their invention are surprisingly soluble in monohydric alcohols in view of the molecular weight of the polymer and the lesser solubility of acrylamide polymers of similar molecular weight. However, the patent acknowledges that solubility of the polymers is not important in the applications comtemplated therein, so long as the polymer is dispersible in the alcohol. Moreover, in Example 9, the patent states that the sodium salt of the homopolymer is dispersed in ethanol.

U.S. Pat. No. 4,412,026 to Collins discloses that an aldehyde containing composition is thickened by the use of salts of polyacrylamidomethylpropanesulfonic acid.

U.S. Pat. No. 4,412,027 to Klein, et al., discloses that salts of polyacrylamidomethylpropanesulfonic acid thickened ketone containing compositions.

SUMMARY OF THE INVENTION

This invention relates to alcoholic antibacterial compositions containing a thickening amount of a polymer having the recurring structural unit:

—(CH$_2$—CH(C(O)NH—R—SO$_3$M))— wherein R is a divalent hydrocarbon group and M is a hydrogen atom or an ammonium group. This invention also relates to methods of thickening an alcoholic antibacterial composition and to the use of the thickened alcoholic antibacterial composition as an antibacterial agent.

DETAILED DESCRIPTION OF THE INVENTION

The alcoholic antibacterial compositions that are thickened for the practice of this invention generally contain one or more alcohols having antibacterial activity. Examples of suitable alcohols are the alkanols having from 1-8 aliphatic hydrocarbon atoms and mixtures thereof. These alkanols can also be used in admixture with aromatic substituted alkanols such as beta-phenethyl alcohol and benzyl alcohol. The alcoholic antibacterial compositions of this invention preferably contain ethanol, propanol and benzyl alcohol as the active ingredients.

The preferred alcoholic antibacterial compositions preferably contain as active ingredients, a major portion (e.g. between about 40% and about 50% by weight) ethanol (wherein the ethanol contains 4% water), a minor portion (e.g. between about 20% and 30% by weight) anhydrous isopropanol, and a nominal amount (e.g. about 0.5% to about 2% by weight) benzyl alcohol.

The alcoholic antibacterial compositions of this invention may also contain hydrogen peroxide as a supplemental antibacterial agent. A preferred example of an alcoholic antibacterial composition which contains hydrogen peroxide as an antibacterial agent is SPITA-DERM ® from Henkel KGaA which is composed of 70% isopropanol, 0.5% chlorohexidinedigluconate, 0.45% hydrogen peroxide and balance water. Alternatively, the hydrogen peroxide may be present in only trace amounts, i.e. as the residue of hydrogen peroxide disinfectant used in sterilizing the equipment and the containers which are used for processing and transporting the alcoholic antibacterial compositions. The amount of hydrogen peroxide in the alcoholic antibacterial composition may therefore range from trace amounts up through about 2% by weight of the composition. Because hydrogen peroxide generates free radicals in solution which cause the degradation of the polymeric thickener over time, the preferred antibacterial compositions contain little or no hydrogen peroxide.

It has also been found that brucine sulfate, a common denaturant for ethanol, will complex with the polymeric thickener over time. The formation of this complex, like the degradation of the polymer by hydrogen peroxide generated free radicals, leads to a slow gradual loss of viscosity over a long period of time. To achieve optimum shelf life, ethanol having a denaturant other than brucine sulfate should be used in the alcoholic compositions of this invention.

The polymeric thickener useful in the present invention is a polymer wherein the major recurring structural unit is derived from an acrylamidoalkanesulfonic acid or an ammonium salt thereof. These polymers are generally described in U.S. Pat. No. 3,692,673 which is incorporated herein by reference thereto. The preferred polymer is obtained by polymerizing amount of a mixture that is at least about 50% by weight of 2-acrylamido-2-methylpropanesulfonic acid or an ammonium salt thereof. The most preferred polymers are homopolymers of 2-acrylamido-2-methylpropanesulfonic acid or an ammonium salt thereof.

The polymer is preferably prepared by means which will provide a polymer having a molecular weight between about 50,000 and about 5,000,000. The molecular weight of the polymer is more preferably greater than about 500,000 and is most preferably greater than about 1,000,000.

To determine the molecular weight of the preferred polymers of this invention, i.e. homopolymers of 2-acrylamido-2-methylpropanesulfonic acid or a salt thereof, the intrinsic viscosity of the polymer can be used in the Mark-Houwink equation:

$$[n] = KM^a$$

wherein [n] is the intrinsic viscosity, M is the molecular weight and K and a are constants for the particular polymer solvent combination. Values of K and a are extensively tabulated in the *Polymer Handbook*, Brandum and Immergent (1975). Because the values of K and a are not tabulated for poly(2-acrylamido-2-methylpropanesulfonic acid), the values for poly(acrylic acid) are used in the Mark-Houwink equation to determine the molecular weight of the preferred homopolymers useful in this invention.

The preferred means of preparing the polymers useful in this invention is by aqueous redox polymerization which may be affected by standard redox polymerization techniques using standard redox catalysts. Examples of suitable redox catalysts include ammonium bisulfite, ferrous sulfate, hydrogen peroxide, and sodium metabisulfite. It is desirable to exclude oxygen from the reaction vessel as it may inhibit the polymerization process. The temperature of the reaction mixture is not critical but should be maintained between about 2° C. and 60° C. The molecular weight of the homopolymer so obtained will range from about 50,000 to about 5,000,000 as determined by its intrinsic viscosity. Chain transfer agents such as mercaptosuccinic acid may be employed in the polymerization reaction to obtain homopolymers of the desired molecular weight.

The amount of polymeric thickener added to the alcoholic antibacterial composition will vary depending upon the amount of thickening desired in the antibacterial composition and the particular molecular weight of the chosen polymeric thickener. In general, the polymeric thickener is added in an amount from about 0.2% to about 2% dry weight of polymeric thickener as a percentage of the weight of the alcoholic antibacterial composition, more preferably from about 0.5% to about 1%.

The polymeric thickener can be added to the alcoholic antibacterial composition in the form of the solution resulting from the solution polymerization of the acrylamido alkanesulfonic acid monomer and/or ammonium salt thereof. The polymeric thickener can also be added as the dried product obtained by drying the solution polymerization product. It has been found that the dry form of both the acid and the ammonium salt of the homopolymers of 2-acrylamido-2-methylpropanesulfonic acid hydrate fully within 15 minutes of their addition to an alcoholic antibacterial composition.

The thickened antibacterial compositions of this invention are useful in controlling the growth of a wide variety of bacteria. These compositions can be used both as antiseptics and as disinfectants. It has been found that the polymeric thickeners useful in this invention provide excellent thickening and body to alcoholic antibacterial compositions. It has also been found that the thickened antibacterial compositions when used as antiseptics impart a very desirable hand feel, even after a water or alcohol rinse.

EXAMPLES

The following examples illustrate the preparation and properties of alcoholic antibacterial compositions thickened in accordance with this invention.

DEFINITIONS

Alcoholic Antibacterial Composition (AAC): A mixture comprised of approximately 46% by weight ethanol (which contains about 4% water and has been denatured), 27% anhydrous isopropanol, 1% benzyl alcohol and balance water, which is available from Henkel KGaA as Spitacid ®.

Polymeric Thickener #1: dried flakes of poly(2-acrylamido-2-methylpropanesulfonic acid) available from the Henkel Corporation as Rheothik 80-11.

Polymeric Thickener #2: dried flakes of poly(ammonium 2-acrylamido-2-methylpropanesulfonate) obtained as disclosed in U.S. Ser. No. 636,647 filed July 31, 1984, now abandoned.

Polymeric Thickener #3: a 15% solids solution of Rheothik TM 80-11 available from the Henkel Corporation.

Comparative Thickener: the dried polymer poly(sodium-2-acrylamido-2-methylpropanesulfonate) obtained by polymerizing sodium-2-acrylamido-2-methylpropane sulfonate by techniques such as those disclosed in U.S. Pat. No. 4,065,422.

EXAMPLE 1

A 2 g sample of Polymeric Thickener #1 were added to 98 g of the AAC, and the resulting solution was stirred on a magnetic stirrer. The polymer dissolved within 10 minutes to yield a very thick solution.

EXAMPLE 2

A 1 g sample of Polymeric Thickener #1 was added to 99 g of the AAC, and was stirred as in Example 1. Within 10 minutes the polymer was completely dissolved to yield a solution that was thinner than the solution of Example 1, but was still very thick.

EXAMPLE 3

A ½ g sample of Polymeric Thickener #1 was added to 99.5 g of the AAC, and was stirred as in Examples 1 and 2. Within 10 minutes the polymeric thickener was completely dissolved to yield a solution with a viscosity desirable in a pourable antiseptic, i.e. a Brookfield viscosity between about 300 and about 400 cps.

EXAMPLE 4

A ½ g sample of Polymeric Thickener #2 was added to 99.5 g of the AAC, and was stirred as in Examples 1-3. Within 5 minutes the Polymeric Thickener was completely dissolved to yield a solution with a viscosity similar to that of Example 3.

EXAMPLE 5

A 3.33 g sample of Polymeric Thickener #3 was added to 96,66 g of the AAC (0.5% Polymeric Thickener on a dry basis) and stirred as in Examples 1-4. The liquid dispersed within one minute to yield a solution having a viscosity similar to that of Examples 3 and 4.

COMPARATIVE EXAMPLE A

A ½ g sample of Polymeric Thickener A was added to 99.5 g of the AAC, and the resulting mixture was stirred on a magnetic stirrer. The Polymeric Thickener did not appear to be soluble in the AAC and did not apreciably thicken the AAC even after two days of continuous mixing.

What is claimed is:

1. A method of controlling the growth of bacteria comprising subjecting bacteria to a bactericidally effective amount of an alcoholic antibacterial composition composed of a mixture of about 40-50% ethanol, about 20-30% isopropanol and about 0.5-2% benzyl alcohol thickened with 0.2-2% by weight of a homopolymer selected from the group consisting of (x) poly(2-acrylamido-2-methylpropane sulfonic acid) and (y) poly(ammonium 2-acrylamido-2-methylpropane sulfonate) wherein said homopolymer has a molecular weight from about 50,000 to about 5,000,000.

2. A method as defined in claim 1 wherein said homopolymer is poly(2-acrylamido-2-methylpropane sulfonic acid).

3. A method as defined in claim 1 wherein said homopolymer is poly(ammonium-2-acrylamido-2-methylpropane sulfonate).

4. A method as defined in claim 1, wherein said homopolymer has a molecular weight of about 1,000,000 to about 2,000,000.

* * * * *